United States Patent [19]

Whitney et al.

[11] 4,117,213

[45] Sep. 26, 1978

[54] ALKALI METAL SALTS OF COMPLEX ANIONS CONTAINING HETEROATOM SUBSTITUENTS AND ELECTROLYTE COMPOSITIONS CONTAINING THESE

[75] Inventors: Thomas A. Whitney, Roselle; Lawrence P. Klemann, Somerville, both of N.J.

[73] Assignee: Exxon Research & Engineering Co., Linden, N.J.

[21] Appl. No.: 870,662

[22] Filed: Jan. 19, 1978

Related U.S. Application Data

[63] Continuation-in-part of Ser. No. 827,132, Aug. 24, 1977, abandoned.

[51] Int. Cl.² ............................................. H01M 6/14
[52] U.S. Cl. ................................... 429/194; 260/299; 260/319.1; 548/335
[58] Field of Search ............... 429/194, 197; 252/62.2; 548/335; 260/299, 300, 319.1, 326.61, 326.9, 313.1

[56] References Cited

U.S. PATENT DOCUMENTS 4,060,674  11/1977  Klemann et al. ................... 429/194

OTHER PUBLICATIONS

Jour. Amer. Chem. Soc., Trofimenko, vol. 89, pp. 3170-3176 and 6288-6294, 1967.

*Primary Examiner*—Charles F. LeFevour
*Attorney, Agent, or Firm*—Kenneth P. Glynn

[57] ABSTRACT

Alkali metal salts of complex anions having heteroatom substituents are described. The compounds are those having the formula:

$$ZMR_xQ_y$$

wherein Z is an alkali metal selected from the group consisting of lithium and sodium, M is a metal selected from the group consisting of Zn, Cd, B, Al, Ga, Sn (stannous), P and As, the Rs are certain organic radicals, the Qs are certain heteroatom substituents, $x$ is zero or a positive integer, and $y$ is a positive integer, subject to the provisos that the sum of $x$ plus $y$ is equal to one plus the valence of the metal M and that, when M is boron, $y$ is one, two or three. Also described are electrolyte compositions which comprise: (a) organic solvents selected from the group consisting of inertly substituted and unsubstituted ethers, esters, sulfones, organic sulfites, organic sulfates, organic nitrates andorganic nitro compounds; and (b) electrolytically active alkali metal salts including alkali metal complex anion salts described above.

47 Claims, No Drawings

ALKALI METAL SALTS OF COMPLEX ANIONS CONTAINING HETEROATOM SUBSTITUENTS AND ELECTROLYTE COMPOSITIONS CONTAINING THESE

CROSS REFERENCE TO RELATED APPLICATIONS

This application is a continuation-in-part of copending application Ser. No. 827,132 filed Aug. 24, 1977 now abandoned.

BACKGROUND OF THE INVENTION

1. Field of the Invention

The present invention relates to novel compounds and more particularly to novel alkali metal salts of complex anions having heteroatom substituents. The present invention is also directed to electrolyte compositions containing certain organic solvents and the mentioned compounds.

2. Prior Art Statement

It is believed that the compounds of the present invention have not been heretofore made or discovered and that no compounds existed heretofore which would render the compounds of the present invention obvious. A prior art statement in support of this position will be submitted within three months from the filing date hereof.

DESCRIPTION OF THE PRESENT INVENTION

The present invention is directed to compounds of the following formula:

$$ZM R_x Q_y \qquad (1)$$

wherein Z is an alkali metal selected from the group consisting of lithium and sodium, M is a metal selected from the group consisting of Zn, Cd, B, Al, Ga, Sn (stannous), P and As, the Rs are inertly substituted and unsubstituted organic radicals, the Qs are heteroatom substituents more specifically described below, $x$ is zero or a positive integer, and $y$ is a positive integer, subject to the provisos that the sum of $x$ plus $y$ is equal to one plus the valence of the metal M and that, when M is boron, z is one, two or three. Preferably, $y$ is one, two or three.

The alkali metal represented by Z in formula (1) above is selected from the group consisting of lithium and sodium, with lithium being the preferred embodiment.

The metal M in Formula (1) is any of zinc, cadmium, boron, aluminum, gallium, tin (stannous), phosphorus and arsenic. Desirably, M is selected from the group consisting of boron, aluminum, phosphorus and arsenic. Most preferred is boron.

The variable R in Formula (1) above occurs $x$ number of times and each R may be the same or different from the other Rs in a given formula. As mentioned, the Rs in general represent inertly substituted and unsubstituted organic radicals. Of these, the unsubstituted radicals are preferred. By "inertly substituted" is meant radicals containing substituents which have no detrimental effect on the formation or stability of the compounds and do not otherwise negate the utility of the compounds. These organic radicals R may be inertly substituted and unsubstituted alkyl radicals and aralkyl radicals. By "aralkyl" is meant an alkyl radical containing a pendant aryl group. It is intended that these alkyl radicals and aralkyl radicals include linear and branched radicals, as well as those in which at least a part of the alkyl moiety may be carbocyclic. The organic radicals R may be selected from the group consisting of alkyl radicals having 1 to 25 carbon atoms, and aralkyl radicals having 7 to 25 carbon atoms. Desirable organic radicals are the alkyl radicals having 1 to 10 carbon atoms and the aralkyl radicals having 7 to 10 carbon atoms. Preferred are the alkyl radicals having 1 to 4 carbon atoms. Particularly useful are the compounds wherein R represents methyl and/or ethyl radicals.

The variable Q represents heteroatom substituents and occurs a sufficient number of times in the compound of the present invention to render a total valence of $y$. In general, Q may represent one or more heteroatom substituents selected from the group consisting of:

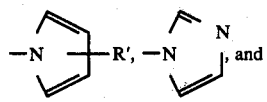

and any dimeric or trimeric composite of the foregoing radicals, and any group composed of two or three of the above structural units linked directly or through additional carbon (as methylene or methine carbon), wherein each R' may be the same or different and is selected from the group consisting of hydrogen and any R as defined above. Preferably, R' is hydrogen.

As mentioned, the variable $x$ in Formula (1) above is zero or a positive integer, $y$ is a positive integer and the sum of $x$ plus $y$ is equal to one plus the valence of the metal M, except that when M is boron, $y$ is one, two or three. Also, as mentioned, $x$ represents the number of organic radicals R which occur in the compound of the present invention, whereas $y$ represents the total valence of the heteroatom substituents Q which are present in the compound. When all of the Qs in the formula are the preferred monoanion substituents, the total valence $y$ also equals the total number of such heteroatom substituents present. However, when polyanion substituents are included, e.g. dianion, trianion, etc., substituents, the total number of such substituents in the compound will be less than $y$.

Nonlimiting examples of the present invention alkali metal salts of complex anions containing heteroatom substituents include:

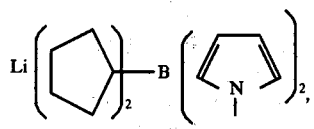

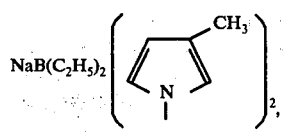

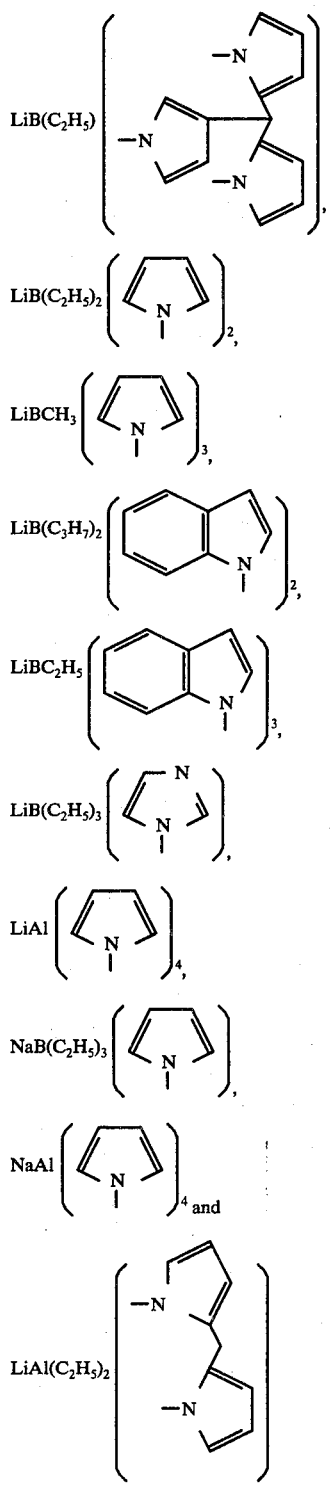

The compounds of the present invention may be prepared by one of a number of techniques. Those compounds containing at least one monovalent heteroatom substituent may be prepared by reacting an alkali metal monovalent heteroatom substituent compound with the metallic or metalloid compound which corresponds to the ultimate present invention compound desired. This reaction may be represented by the following equation:

$$ZQ + MR_xQ_{y-1} \rightarrow ZMR_xQ_y \quad (A)$$

wherein ZQ is an alkali metal monovalent heteroatom substituent compound and all other variables as described above.

Those compounds of the present invention which contain at least one organic radical substituent R may be prepared by reacting an alkali metal organo compound with the metallic or metalloid compound which corresponds to the ultimate present invention compound which is desired. This particular reaction may be represented by the following equation:

$$ZR + MR_{x-1}Q_y \rightarrow ZMR_xQ_y \quad (B)$$

wherein all of the variables are as defined above.

Compounds of the present invention which may be prepared by the technique such as that illustrated in Equation (A) above may alternatively be prepared by using an alkali metal hydride or alkali metal amide in place of the alkali metal salt ZQ according to the following equations:

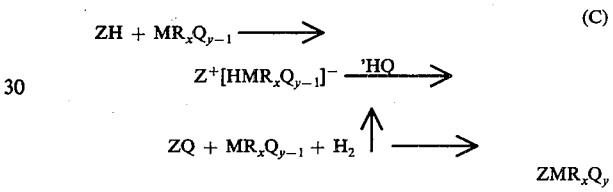

and

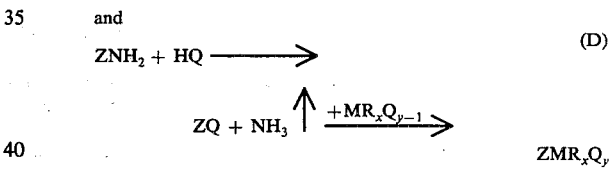

wherein the variables are as defined above. In fact, for the sodium compounds, the method represented by the reactions set forth in Equation (C) is preferred.

Compounds of the present invention containing both organic radical substituents and monovalent (monoanionic) heteroatom substituents may be prepared by any of the above techniques.

Compounds of the present invention containing neither organic substituent R nor monovalent heteroatom substituent Q, i.e. compounds of the present invention containing only polyanion heteroatom substituents, may be prepared by nucleophilic substitution on the metal or metalloid M. For example, the following reaction is typical:

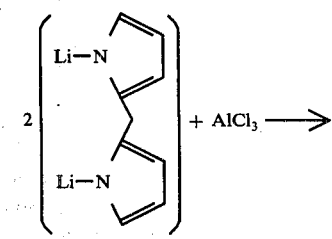

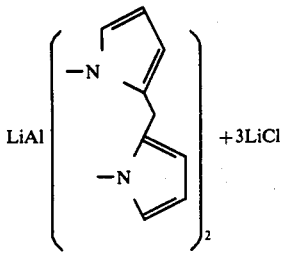

The above reactions may be carried out at any operable pressure and temperature, and room temperature and pressure conditions will allow the reaction to readily occur in most instances. Desirably, the reactions are carried out at about −100° to about 150° C., and preferably at about −20° to about 80° C., e.g. room temperature. In general, any compatible organic solvent may be used as a vehicle for the above reactions. Typical among these are hydrocarbons such as pentane, heptane, benzene, toluene, etc., and ethers such as diethyl ether, tetrahydrofuran and dimethoxyethane and the like. Other compatible solvents may be within the purview of the artisan.

The present invention is also directed to electrolyte compositions containing the above compounds as represented by Formula (1). More specifically, the electrolyte compositions of the present invention comprise organic solvent and electrolytically active alkali metal salts including an alkali metal heteroatom substituted complex anion salt of Formula (1) above. Thus, a mixture of salts is contemplated, at least one of which is a Formula (1) type. The other salt or salts in the mixture may be any electrolytically active alkali metal salt which is compatible with the Formula (1) type compound, e.g. LiBr, LiI and the like. Also contemplated is the electrolyte which contains only one or more salts of Formula (1). Thus, the expression "electrolytically active alkali metal salts including an alkali metal heteroatom substituted complex anion salt" should be construed to include: (1) mixtures of alkali metal heteroatom substituted complex anion salt(s) and other compatible alkali metal salt(s), and (2) one or more alkali metal heteroatom substituted complex anion salts without other salts. Preferred is the electrolyte containing the heteroatom substituted complex anion salt(s) without other salts.

The organic solvent employed in the electrolyte composition of the present invention is generally one selected from the group consisting of inertly substituted and unsubstituted ethers, esters, sulfones, organic sulfites, organic sulfates, organic nitrites and organic nitro compounds. By "inertly substituted" solvent is meant one which contains substituents which have no detrimental effect on the electrolytic properties of the electrolyte composition in the context of its effectiveness in electrochemical cells. These solvents may be any of the foregoing which will function as either a diluent or as a complexing solvent with the organometallic alkali metal salt and which will, with the salt, produce an effective electrolyte. Thus, the solvents which are included are those composed of one or more compounds selected from straight chain ethers, polyethers, and cyclical ethers; including such ethers as the acetals, ketals, and ortho-esters; and organic esters, sulfones, organic nitro compounds and nitrites and organic sulfates and sulfites. Examples include propylene carbonate, tetrahydrofuran, dioxolane, furan, sulfolane, dimethyl sulfite, nitrobenzene, nitromethane and the like. The preferred solvents are the ethers. For example, dioxolane, dimethoxyethane, and mixtures of these are useful. Preferred is a solvent containing dioxolane.

In general, sufficient organic solvent must be utilized to effectively render the organometallic alkali metal salt electrolytically active (i.e., adequately conductive) when employed in an electrolytic cell. The solvent may be a mixture of compounds as suggested above, and may contain known electrolyte additives which are compatible with the solvent and the particular salt employed. As to the amount of salt to be employed in the organic solvent, this will vary tremendously with the specific solvent used, the salt chosen and the type of electrochemical cell performance which is desired. In any event, an electrolytically active amount of salt must be added to the solvent. Typically, at least about 0.01 molal of salt up to saturation may be used, e.g., about 0.01 to about 10 molal may be used and preferably about 0.5 to about 3 molal may be used.

The following examples are presented as merely illustrative of the present invention, and the invention should not be construed to be limited thereto:

EXAMPLE 1

N-lithiopyrrole is prepared by the addition of n-butyl lithium to a solution of pyrrole in pentane at room temperature. The suspension is then filtered and the solid is washed with pentane and dried under a nitrogen flow to constant weight. Solutions of

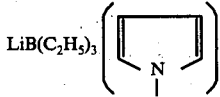

are prepared in pure dioxolane and 70/30 dioxolane-dimethoxyethane by adding solid N-lithiopyrrole to solutions of $B(C_2H_5)$ to make the 1:1 salt. $^1H$ NMR analysis confirms the formation of the compound: $C_2H_5$ resonances: complex multiplet from $\delta 0.6$ to $1.5$ centered at $\delta 1.1$; pyrrole resonances: triplet at $\delta 6.4$ $J = 1.8$ and triplet at $\delta 7.35$ $J = 1.8$. The triethyl boron resonances of the product salt are completely consistant with complex anion formation based on the NMR spectrum of a triethyl boron reference.

EXAMPLE 2

In order to test the electrolytic capability of the compound obtained in Example 1, the compound is dissolved in pure dioxolane at various concentrations and the resistivities of the solutions are measured using a Barnstead Model PM-70CB Conductivity Bridge and a Yellow Springs Instrument Co. Model YSI 3403 Cell having platinum electrodes and having a cell constant of 1.0. The results presented in Table I establish very low resistivity at the various concentrations tested.

TABLE I

Resistivity of LiB(C₂H₅)₃ In Dioxolane [pyrrole structure]

| Concentration (molal) | Resistivity (ohm-cm) |
|---|---|
| 1.0 | 140 |
| 1.5 | 134 |
| 2.0 | 156 |
| 2.5 | 204 |
| 3.0 | 296 |

EXAMPLE 3

The compound of Example 1 is again tested in accordance with the procedure of Example 2, except that a dioxolane-dimethoxyethane solvent is used. The resistivity is found to be very low as shown in Table II:

TABLE II

Resistivity of LiB(C₂H₅)₃ In Dioxolane-Dimethoxyethane (70/30, V/V) [pyrrole structure]

| Concentration (molal) | Resistivity (ohm-cm) |
|---|---|
| 1.0 | 92 |
| 1.5 | 95 |
| 2.0 | 116 |
| 2.5 | 153 |
| 3.0 | 229 |

EXAMPLE 4

N-lithioindole is prepared in accordance with the procedure of Example 1. Solutions of

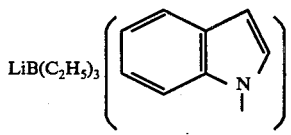

LiB(C₂H₅)₃ [indole structure]

are prepared in pure dioxolane and 70/30 dioxolane-dimethoxyethane by adding solid N-lithioindole to solutions of B(C₂H₅)₃ to make the 1:1 salt. ¹H NMR analysis confirms the formation of the compound based on reference spectra of the components.

EXAMPLE 5

The compound of Example 4 is tested in accordance with Example 2. Table III, below, shows the data obtained.

TABLE III

Conductivity of LiB(C₂H₅)₃ in Dioxolane [indole structure]

| Concentration (molal) | Resistivity (ohm-cm) |
|---|---|
| 0.5 | 220 |
| 1.0 | 155 |
| 1.5 | 168 |
| 2.0 | 216 |

TABLE III-continued

Conductivity of LiB(C₂H₅)₃ in Dioxolane [indole structure]

| Concentration (molal) | Resistivity (ohm-cm) |
|---|---|
| 2.5 | 403 |

EXAMPLE 6

The compound of Example 4 is tested in accordance with Example 3. The data are shown in Table IV.

TABLE IV

Conductivity of LiB(C₂H₅)₃ in Dioxolane-Dimethoxyethane (70/30, V/V) [indole structure]

| Concentration (molal) | Resistivity (ohm-cm) |
|---|---|
| 0.24 | 255 |
| 0.5 | 166 |
| 1.0 | 124 |
| 1.5 | 134 |
| 2.0 | 177 |
| 2.5 | 286 |

EXAMPLE 7

A 1.56 g (22.9 mmoles) portion of imidazole is dissolved in 100 ml of tetrahydrofuran and the solution is cooled to −60° C. and 10 ml (22.9 mmoles) of n-C₄H₉Li solution in hexane is added dropwise with stirring. The reaction mixture is then allowed to warm to room temperature over 75 minutes. The reaction mixture is then filtered through a fritted disk (ASTM 10-15) and a white solid lithium salt of imidazole (lithioimidazole-A) is isolated, dried weight 1.1g.

The filtrate is evaporated to dryness under high vacuum and lithioimidazole-B is recovered, wt. 1.04 g.

That both products are lithium salts of imidazole is confirmed by ¹H and ¹³C NMR analysis based on reference spectra as well as by hydrolysis of both products in D₂O with the regeneration of imidazole as determined by NMR.

Solutions of LiB(C₂H₅)₃[lithioimidazole-A] and LiB(C₂H₅)₃[lithioimidazole-B] are prepared in dioxolane using 1:1 mole ratios of B(C₂H₅)₃ and lithioimidazole-A and lithioimidazole-B respectively. NMR analysis confirms the formation of the compounds based on reference spectra of the components.

EXAMPLE 8

LiB(C₂H₅)₃[lithioimidazole-A] in dioxolane is tested in accordance with Example 2. Table V illustrates the data obtained.

TABLE V

Conductivity of LiB(C₂H₅)₃[lithioimidazole-A] in Dioxolane

| Concentration (molal) | Resistivity (ohm-cm) |
|---|---|
| 0.5 | 840 |
| 1.0 | 557 |
| 1.5 | 560 |

TABLE V-continued

| Conductivity of LiB(C₂H₅)₃[lithioimidazole-A] in Dioxolane | |
|---|---|
| Concentration (molal) | Resistivity (ohm-cm) |
| 2.0 | 710 |

EXAMPLE 9

LiB(C₂H₅)₃[lithioimidazole-B] in dioxolane is tested in accordance with Example 2. Table VI sets forth the results obtained.

TABLE VI

| Conductivity of LiB(C₂H₅)₃[lithioimidazole-B] in Dioxolane | |
|---|---|
| Concentration (molal) | Resistivity (ohm-cm) |
| 0.54 | 262 |
| 1.17 | 225 |
| 1.23 | 230 |

EXAMPLE 10

In an N₂ dry box, an excess of NaH in oil (6 g) is washed on a sintered glass funnel with 400 ml of pentane. The solid NaH is then transferred to an Erlenmeyer flask with 40 ml of dioxolane. A solution of triethylboron (19.6 g, 0.2 mole) in 30 ml of dioxolane is then added slowly with stirring. An exothermic reaction is observed. After this addition is complete, stirring is continued for 30 minutes at room temperature and the mixture is filtered. The residual NaH is washed with 15 ml of dioxolane and the washings are added to the filtrate. To the filtrate is then added, dropwise over 45 minutes, a solution of pyrrole (13.4 g, 0.2 mole) in 30 ml of dioxolane. Vigorous gas evolution is observed during the addition. After this addition is complete, stirring is continued for 1.5 hours. A sample of this solution is then analyzed by NMR. Comparison of the chemical shifts for the ethyl protons with a B(C₂H₅)₃ standard in dioxolane support formation of NaB(C₂H₅)₃(C₄H₄N). Integration shows the solute concentration to be 2.0 moles per liter of dioxolane. This solution and subsequent dilutions derived from it, are measured for their specific resistivities: molal (ohm cm): 2.0 (210), 1.5 (204), 1.0 (230), and 0.75 (267).

EXAMPLE II

The following general method of construction is used to prepare cells for use in testing of electrolytes containing the novel compositions set forth above.

The test cells contain a lithium or sodium anode prepared by pressing alkali metal ribbon onto expanded tantalum screen. The cathode is a porous cake of a mixture of TiS₂ and Teflon (90-95% TiS₂ and 5-10% Teflon) pressed onto an expanded tantalum screen. The anode and cathode are fitted into microporous polypropylene bags sold under the name Celgard by Celanese Corporation of America, New York. A glass mat is placed between the anode and cathode. Each cell also contains a reference alkali metal electrode constructed by pressing the appropriate alkali metal onto expanded tantalum screen. The reference electrode is fitted into a microporous polypropylene bag and separated from the adjacent cathode by means of a glass mat. In the completed cell the reference electrode is located on one side of the cathode while the anode is located on the opposite side.

Into one such cell containing a lithium anode and a TiS₂ cathode containing a weight of active material so as to provide 96.7 mA Hr. of theoretical capacity, is placed the electrolyte of Example 4 containing 2.0 moles of

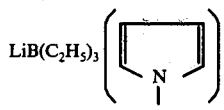

per liter of dioxolane. This cell is discharged at a current of 64 mA to afford utilization of 87 mAHr capacity at the end of the first discharge. The cell is then recharged at 16 mA.

The discharge cycle is then repeated. After 10 discharge/charge cycles the accumulated capacity drawn from the cell is 822 mA Hr. This demonstrates the rechargeable character of the battery, and the ability of the novel solute composition to function as a non-aqueous electrolyte in dioxolane.

EXAMPLE 12

Lithium aluminum hydride (1.14 g, 30 mmole) is suspended in 30 ml of dioxolane under a dry N₂ atmosphere. Pyrrole (9 g, 134 mmole) is added dropwise and vigorous gas evolution is observed. After stirring one hour, the mixture is filtered. The specific resistivity of the filtrate is 178 ohm cm. The ¹H NMR spectrum of this solution is consistant with a 0.95 molal concentration of

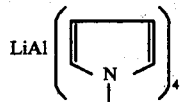

in dioxolane. The filtrate is stripped to give 19.9 g of crude crystalline product containing dioxolane. The product is washed with n-heptane and dried under high vacuum with heating affording a product weighing 12.5 g.

What is claimed is:

1. A compound having the formula:

ZMR$_x$Q$_y$ wherein Z is an alkali metal selected from the group consisting of lithium and sodium;
   wherein M is a metal selected from the group consisting of Zn, Cd, B, Al, Ga, Sn (stannous), P, and As;
   wherein R represents radicals which may be the same or different and are inertly substituted or unsubstituted organic radicals selected from the group consisting of alkyl radicals having 1 to 25 carbon atoms, and aralkyl radicals having 7 to 25 carbon atoms;
   wherein Q represents heteroatom substituents selected from the group consisting of:

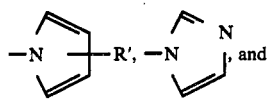

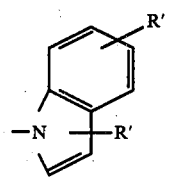

and any dimeric or trimeric composite of the foregoing radicals, and any group composed of two or three of the above structural units linked directly or through an additional carbon, wherein R' may be the same or different and is selected from the group consisting of hydrogen and any R as defined above;

wherein $x$ is zero or a positive integer and equals the total number of R radicals present; and wherein $y$ is a positive integer and equals the total valence of all Q radicals present, subject to the provisos that the sum of $x$ plus $y$ is equal to one plus the valence of the metal M, and that when M is boron, $y$ is equal to one, two or three.

2. The compound of claim 1 wherein said metal M is selected from the group consisting of B, Al, P and As.

3. The compound of claim 2 wherein the organic radicals R are selected from the group consisting of alkyl radicals having 1 to 10 carbon atoms and aralkyl radicals having 7 to 10 carbon atoms.

4. The compound of claim 3 wherein the R' radicals are selected from the group consisting of hydrogen, alkyl radicals having 1 to 10 carbon atoms and aralkyl radicals having 7 to 10 carbon atoms.

5. The compound of claim 4 wherein $y$ is equal to one, two or three.

6. The compound of claim 5 wherein said metal is boron.

7. The compound of claim 6 wherein the organic radicals R are selected from the group consisting of alkyl radicals having 1 to 4 carbon atoms.

8. The compound of claim 7 wherein the organic radicals R are selected from the group consisting of methyl and ethyl.

9. The compound of claim 8 wherein the R' radicals are selected from the group consisting of hydrogen, methyl and ethyl.

10. The compound of claim 9 wherein the R' radicals are hydrogen.

11. The compound of claim 1 wherein said alkali metal is lithium.

12. The compound of claim 11 wherein said metal M is selected from the group consisting of B, Al, P and As.

13. The compound of claim 12 wherein the organic radicals R are selected from the group consisting of alkyl radicals having 1 to 10 carbon atoms and aralkyl radicals having 7 to 10 carbon atoms.

14. The compound of claim 13 wherein the R' radicals are selected from the group consisting of hydrogen, alkyl radicals having 1 to 10 carbon atoms and aralkyl radicals having 7 to 10 carbon atoms.

15. The compound of claim 14 wherein $y$ is equal to one, two or three.

16. The compound of claim 15 wherein said metal is boron.

17. The compound of claim 16 wherein the organic radicals R are selected from the group consisting of alkyl radicals having 1 to 4 carbon atoms.

18. The compound of claim 17 wherein the organic radicals R are selected from the group consisting of methyl and ethyl.

19. The compound of claim 18 wherein the R' radicals are selected from the group consisting of hydrogen methyl and ethyl.

20. The compound of claim 19 wherein the R' radicals are hydrogen.

21. An electrolyte composition comprising:
(a) an organic solvent selected from the group consisting of inertly substituted and unsubstituted ethers, sulfones, organic sulfates, organic sulfites, organic nitrites and organic nitro compounds; and having dissolved therein:
(b) electrolytically active alkali metal salts including an electrolytically active amount of an alkali metal salt having the formula:

$$ZMR_xQ_y$$

wherein Z is an alkali metal selected from the group consisting of lithium and sodium;

wherein M is a metal selected from the group consisting of Zn, Cd, B, Al, Ga, Sn (stannous), P, and As;

wherein R represents radicals which may be the same or different and are inertly substituted or unsubstituted organic radicals selected from the group consisting of alkyl radicals having 1 to 25 carbon atoms, and aralkyl radicals having 7 to 25 carbon atoms;

wherein Q represents heteroatom substituents selected from the group consisting of:

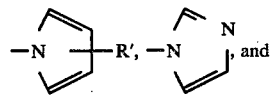

and any dimeric or trimeric composite of the foregoing radicals, and any group composed of two or three of the above structural units linked directly or through an additional carbon, wherein each R' may be the same or different and is selected from the group consisting of hydrogen and any R as defined above;

wherein $x$ is zero or a positive integer and equals the total number of R radicals present; and wherein $y$ is a positive integer and equals the total valence of all Q radicals present, subject to the provisos that the sum of $x$ plus $y$ is equal to one plus the valence of the metal M, and that when M is boron, $y$ is equal to one, two or three.

22. The electrolyte composition of claim 21 wherein said organic solvent is one or more ethers.

23. The electrolyte composition of claim 22 wherein said metal M is selected from the group consisting of B, Al, P and As.

24. The electrolyte composition of claim 23 wherein the organic radicals R are selected from the group consisting of alkyl radicals having 1 to 10 carbon atoms and aralkyl radicals having 7 to 10 carbon atoms.

25. The electrolyte composition of claim 24 wherein the R' radicals are selected from the group consisting of hydrogen, alkyl radicals having 1 to 10 carbon atoms and aralkyl radicals having 7 to 10 carbon atoms.

26. The electrolyte composition of claim 25 wherein $y$ is equal to one, two or three.

27. The electrolyte composition of claim 26 wherein said metal M is boron.

28. The electrolyte composition of claim 26 wherein the organic radicals R are selected from the group consisting of alkyl radicals having 1 to 4 carbon atoms.

29. The electrolyte composition of claim 28 wherein the radicals R are selected from the group consisting of methyl and ethyl.

30. The electrolyte composition of claim 29 wherein the R' radicals are selected from the group consisting of methyl and ethyl.

31. The electrolyte composition of claim 30 wherein the R' radicals are hydrogen.

32. The electrolyte composition of claim 31 wherein the solvent contains dioxolane.

33. The electrolyte composition of claim 32 wherein the concentration of the alkali metal salt in said solvent is about 0.01 to about 10 molal.

34. The electrolyte composition of claim 33 wherein the concentration of the alkali metal salt in said solvent is about 0.5 to about 3 molal.

35. The electrolyte composition of claim 21 wherein said alkali metal is lithium.

36. The electrolyte composition of claim 35 wherein said organic solvent is one or more ethers.

37. The electrolyte composition of claim 36 wherein said metal M is selected from the group consisting of B, Al, P and As.

38. The electrolyte composition of claim 37 wherein the organic radicals R are selected from the group consisting of alkyl radicals having 1 to 10 carbon atoms and aralkyl radicals having 7 to 10 carbon atoms.

39. The electrolyte composition of claim 38 wherein the R' radicals are selected from the group consisting of hydrogen, alkyl radicals having 1 to 10 carbon atoms and aralkyl radicals having 7 to 10 carbon atoms.

40. The electrolyte composition of claim 39 wherein $y$ is equal to one, two or three.

41. The electrolyte composition of claim 40 wherein said metal M is boron.

42. The electrolyte composition of claim 41 wherein the organic radicals R are selected from the group consisting of alkyl radicals having 1 to 4 carbon atoms.

43. The electrolyte composition of claim 42 wherein the radicals R are selected from the group consisting of methyl and ethyl.

44. The electrolyte composition of claim 43 wherein the R' radicals are selected from the group consisting of methyl and ethyl.

45. The electrolyte composition of claim 44 wherein the R' radicals are hydrogen.

46. The electrolyte composition of claim 45 wherein the solvent contains dioxolane.

47. The electrolyte composition of claim 46 wherein the concentration of the alkali metal salt in said solvent is about 0.01 to about 10 molal.

* * * * *

UNITED STATES PATENT OFFICE
CERTIFICATE OF CORRECTION

Patent No. 4,117,213  Dated Sept. 26, 1978

Inventor(s) Thomas A. Whitney, et al

It is certified that error appears in the above-identified patent and that said Letters Patent are hereby corrected as shown below:

In column 7, line 5, the formula $LiB(C_2H_5)_3$  should read as follows: $LiB(C_2H_5)_3$  .

Signed and Sealed this

Eighth Day of May 1979

[SEAL]

Attest:

RUTH C. MASON
Attesting Officer

DONALD W. BANNER
Commissioner of Patents and Trademarks